United States Patent
O'Geary

(10) Patent No.: US 6,609,257 B1
(45) Date of Patent: Aug. 26, 2003

(54) DEBRIDEMENT AND IRRIGATION EXTREMITY BASIN

(75) Inventor: Daniel R. O'Geary, Albuquerque, NM (US)

(73) Assignee: Fiore Industries, Inc., Albuquerque, NM (US)

( * ) Notice: Subject to any disclaimer, the term of this patent is extended or adjusted under 35 U.S.C. 154(b) by 0 days.

(21) Appl. No.: 09/993,867

(22) Filed: Nov. 5, 2001

Related U.S. Application Data

(60) Provisional application No. 60/245,435, filed on Nov. 3, 2000.

(51) Int. Cl.[7] ............................................. E03C 1/264
(52) U.S. Cl. ................. 4/652; 4/289; 4/290; 4/292; 4/516; 4/519; 4/619; 4/621; 4/650
(58) Field of Search ............................ 4/619, 621, 622, 4/640, 650, 652, 653, 515, 516, 519, 520, 523, 289, 290, 292

(56) References Cited

U.S. PATENT DOCUMENTS

| | | | |
|---|---|---|---|
| 2,507,630 A | * 5/1950 | Green ............................ | 4/520 |
| 2,709,435 A | * 5/1955 | Kress ............................ | 4/621 |
| 3,788,485 A | * 1/1974 | Bruning ......................... | 4/292 |
| 4,134,162 A | * 1/1979 | Sharland et al. ................ | 4/292 |
| 4,471,497 A | * 9/1984 | Riutort et al. .................. | 4/292 |
| 4,512,043 A | * 4/1985 | Nolan ........................... | 4/516 |
| 4,658,449 A | * 4/1987 | Martin .......................... | 4/292 |
| 4,771,487 A | * 9/1988 | Little ........................... | 4/519 |
| 5,381,562 A | 1/1995 | Holloway et al. | |
| D398,075 S | 9/1998 | Book et al. | |
| 5,842,238 A | 12/1998 | Herrick et al. | |
| 5,961,733 A | * 10/1999 | Strange ......................... | 134/10 |
| 6,315,896 B1 | * 11/2001 | Johnson ......................... | 4/292 |

\* cited by examiner

Primary Examiner—Tuan N. Nguyen
(74) Attorney, Agent, or Firm—Katy C. Fain; Deborah A. Peacock

(57) ABSTRACT

A basin generally for use in health-care industries for debridement and/or irrigation of wound areas. The basin is best used for treatment of wounds on extremities and comprises a stable basin having contoured seats on opposing side walls and a filtering device to prevent clogging of the drainage hole and tubing.

21 Claims, 4 Drawing Sheets

DEBRIDEMENT AND IRRIGATION EXTREMITY BASIN

CROSS-REFERENCE TO RELATED APPLICATIONS

This application claims the benefit of the filing of U.S. Provisional Patent Application Serial No. 60/245,435, entitled "Debridement and Irrigation Extremity Basin", filed on Nov. 3, 2000, and the specification thereof is incorporated herein by reference.

BACKGROUND OF THE INVENTION

1. Field of the Invention (Technical Field)

The present invention relates to basins for use in medical or hospital facilities, specifically portable basins for holding liquids and tissues resulting from cleansing and treating wounds.

2. Background Art

Basins are commonly used in hospitals and other medical facilities for receipt of body fluids and/or irrigation fluids resulting from wound care. Typically, basins are of two distinct types: fixed or portable. Fixed basins are generally found incorporated into a sink fixture and may be suitable for use for treating a person without particular mobility limitations.

Portable basins are also common in the health-care industry (e.g., emesis basins), and may be used for wound irrigation. Generally, portable basins are usually plastic, bowl-or box-shaped receptacles for receipt of fluids. These basins typically are not engineered for patient comfort in that they do not contain a limb-or body-part supporting upper surface to reduce pressure on the limb or body part.

U.S. Pat. No. 5,381,562 to Holloway et al. discloses a basin for use in irrigation of a wound which includes a limb supporting contour in one wall of the upper surface. However, the Holloway et al. device and other basins known to the art do not include an additional contour in the opposing wall. In using a basin with only one contoured side, the limb or body part may rest on the contour, but must then protrude above the basin otherwise unsupported. In some cases, the location of the wound may require the limb to be additionally extended beyond the opposing side. In such cases, the limb will rest on the uncontoured opposing side, and the patient may experience discomfort in contacting the non-supporting opposing wall surface. Therefore, there is a need in the art for a basin with supporting, contoured sides on opposing walls.

Additionally, typical prior art basins do not provide for drainage or recirculation of fluids received within the basin. Therefore, if a large amount of fluid accumulated in the treatment process, the wound can be reintroduced to flushed fluids. The Holloway et al. device does provide for a drainage hole and tube located in the center of the bottom of its device. However, in many debridement procedures, bits of tissue may disassociate from the wound and be flushed into the basin. The accumulated tissue can clog a drain tube and/or hole, thereby removing its usefulness. The Holloway et al. device has no clog prevention measures. Therefore, there is a need in the art for a basin which prevents clogging of drainage members.

SUMMARY OF THE INVENTION (DISCLOSURE OF THE INVENTION)

The present invention is of a basin, generally used in health-care industries, for treatment of wounds by debridement and/or irrigation. In the preferred embodiment, the basin comprises a receptacle of unitary construction for containing effluent and debris. The receptacle preferably has a contoured seat on the upper surface of its side walls, most preferably two contoured seats on opposing sides of the upper surface. Additionally, the basin preferably contains a filtering device to prevent clogging of a drainage hole and/or tubing. The filtering device may also be of such efficacy as to allow recirculation of irrigation fluid in extreme circumstances where sufficient fluid is unavailable. The filtering device preferably comprises a screen and/or a microfilter placed over the drainage hole. A disengaging member may assist in removal of the filtering device from the basin without contacting the contaminated device.

One embodiment of the basin comprises a unitary fluid and debris receptacle, a drainage hole, and a filtering device covering the drainage hole. Alternate embodiments may omit the filtering device and incorporate at least two contoured seats on opposing sides of the upper surface of the side walls of the receptacle. The basin of the present invention may incorporate both the filtering device and the opposing contoured seats. However, a filtering device may be utilized with only one contoured seat.

The filtering device of the present invention preferably incorporates a screen and/or a microfilter. The microfilter pad may be contained within a holder. The screen preferably comprises apertures between approximately 0.01 cm and approximately 1 cm in width, but most preferably between approximately 0.01 cm and approximately 0.5 cm in width. The microfilter pad preferably comprises apertures between approximately 0.0001 cm and approximately 0.1 cm in width, but preferably between approximately 0.01 cm and approximately 0.05 cm in width. Microfilter pads suitable for recirculation preferably comprise apertures between approximately 0.0001 and approximately 0.05 cm in width.

The unitary fluid and debris receptacle is preferably formed from plastic resins, stainless metals (preferably stainless steel), or fiberglass.

A primary object of the present invention is to provide a basin with opposing, contoured, supporting sides.

Another object of the present invention is to provide a basin which prevents clogging of drainage tubing or holes.

An additional object of the present invention is to provide a stable basin for debridement and irrigation treatments.

A further object of the present invention is to provide a basin with a filter and/or screen member that prevents tissue and debris blockage of drain holes and/or tubing which is easily cleanable.

Yet another object of the present invention is to provide a basin comprising a filter suitable for fluid recirculation.

A further object of the present invention is to provide a basin suitable for incorporation into or use in conjunction with an ultrasonic cleaner.

Another object of the present invention is to provide a disposable basin.

A primary advantage of the present invention is the reduced stresses on a patient's body part during treatment.

Another advantage of the present invention is the prevention of clogging of drainage members with disassociated tissue and debris, thereby reducing risk of contact with such matter.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS (BEST MODES FOR CARRYING OUT THE INVENTION)

The present invention is of an improved portable basin. The invention is stable for use in medical procedures, such as irrigation and debridement, and will resist tipping. It preferably employs drainage members for removal of fluid from its interior as well as filtering components to prevent clogging the drainage members. Further, the device preferably has at least one, and most preferably at least two, contoured seat formed in the upper surface of the basin.

Figure 1:
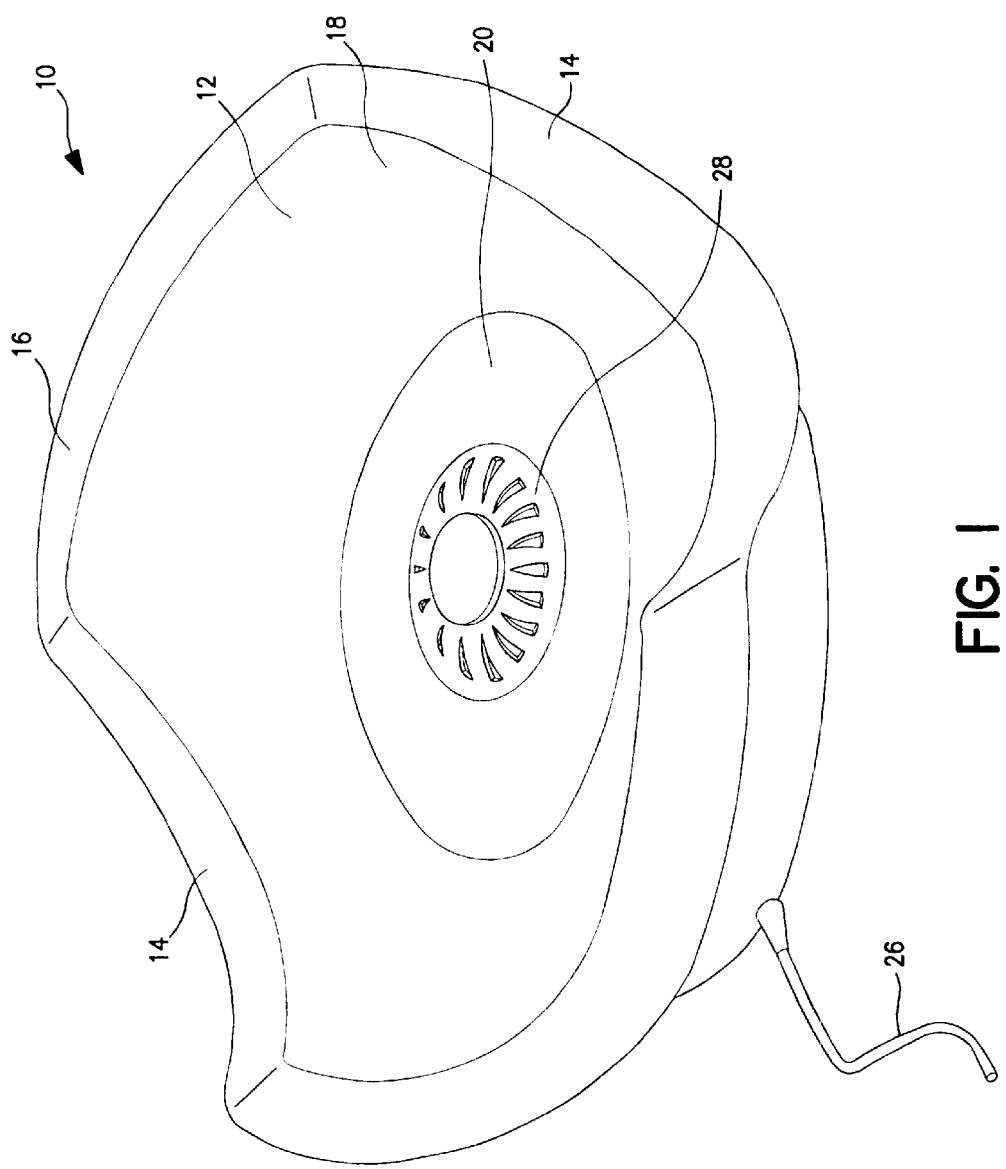
FIG. 1 is a top perspective view of the preferred basin of the invention, depicting the debris screen in place in the base of the basin and further depicting seats within the sidewalls of the invention.

Turning now to the drawings, FIG. 1 depicts the preferred basin 10, preferably having rounded sidewall profile 12 of unitary construction. Alternate embodiments of the invention may have planar sidewalls, however, it is preferred that at least the interior walls of the apparatus be curved. Basin 10 has seats 14 formed in upper surface 16 of sidewall 12. Basin 10 is preferably comprised of a plastic resin, stainless metal, or fiberglass material, however, other materials known to the art may be utilized. Interior surface 18 of basin 10 is preferably smooth and either decreases in width or is curved to form a bowl-shaped bottom 20 of interior surface 18. The bowl shape of the preferred embodiment, or a decreasing diameter of alternate embodiments, uses a gravity flow to guide effluent materials toward drain hole 24. Tubing 26 inserts into drain hole 24, allowing effluent 22 to exit basin 10 through use of gravity or otherwise assisted (e.g. vacuum) flow. Preferably, tubing 26 is attached to a biohazard receptacle for contact-free disposal.

Figure 2:
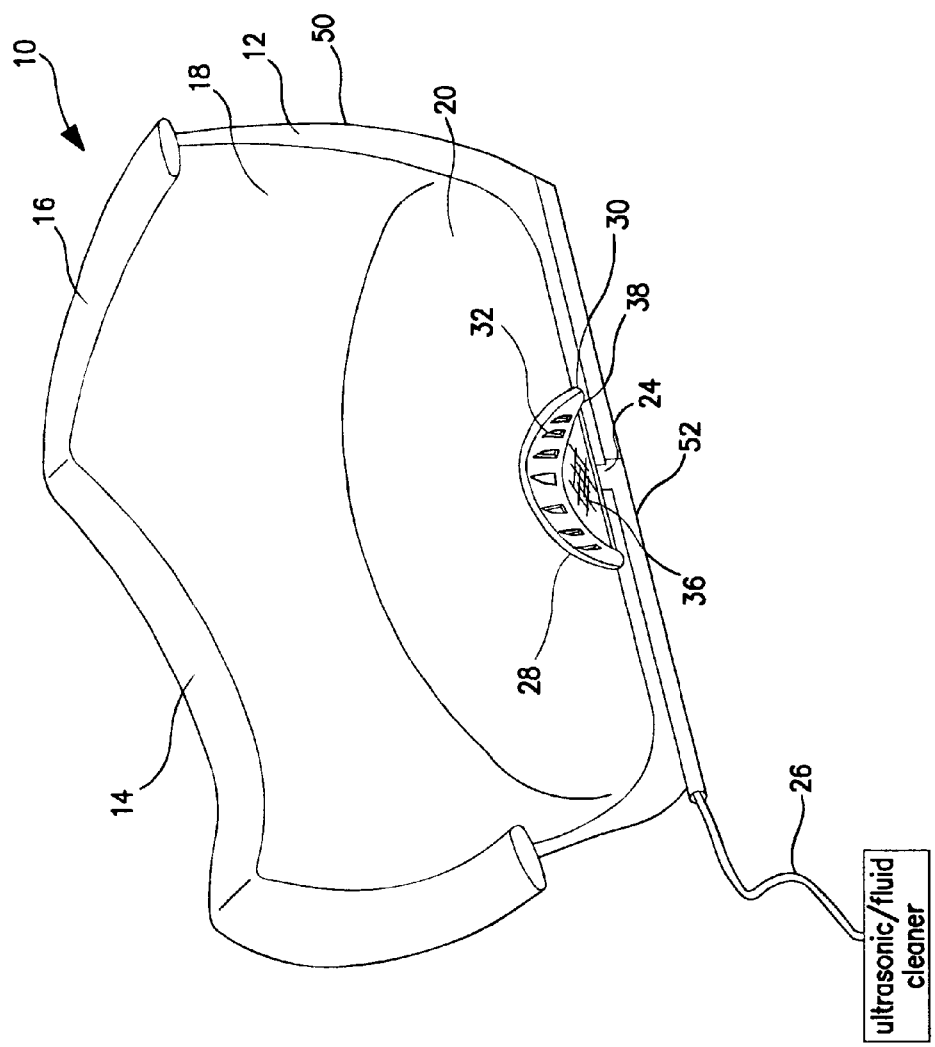
FIG. 2 is a transverse cross-section of the basin depicting use of a screen and microfilter and a contoured seat.

As seen in FIG. 2, debris screen 28 is fittingly placed in groove 30 for a snap-in-place fit over drain hole 24. Screen 28 has apertures 32 to prevent large pieces of debris 34 from entering or blocking drain hole 24. Apertures 32 of screen 28 are preferably between approximately 0.01 cm and approximately 1 cm in width, most preferably between approximately 0.01 cm and approximately 0.5 cm. Microfilter pad 36 is preferably installed within inner surface 38 of screen 28. Apertures of microfilter pad 36 are preferably between approximately 0.0001 cm and approximately 0.1 cm in width, and most preferably between approximately 0.01 cm and approximately 0.05 cm in width to prevent clogging of drain 24 and tubing 26. Additionally, when using basin 10 of the present invention in combination with ultrasonic or other fluid cleaners, apertures of microfilter pad 36 are preferably between approximately 0.0001 cm and approximately 0.05 cm in width for fluid recirculation.

Figure 3:
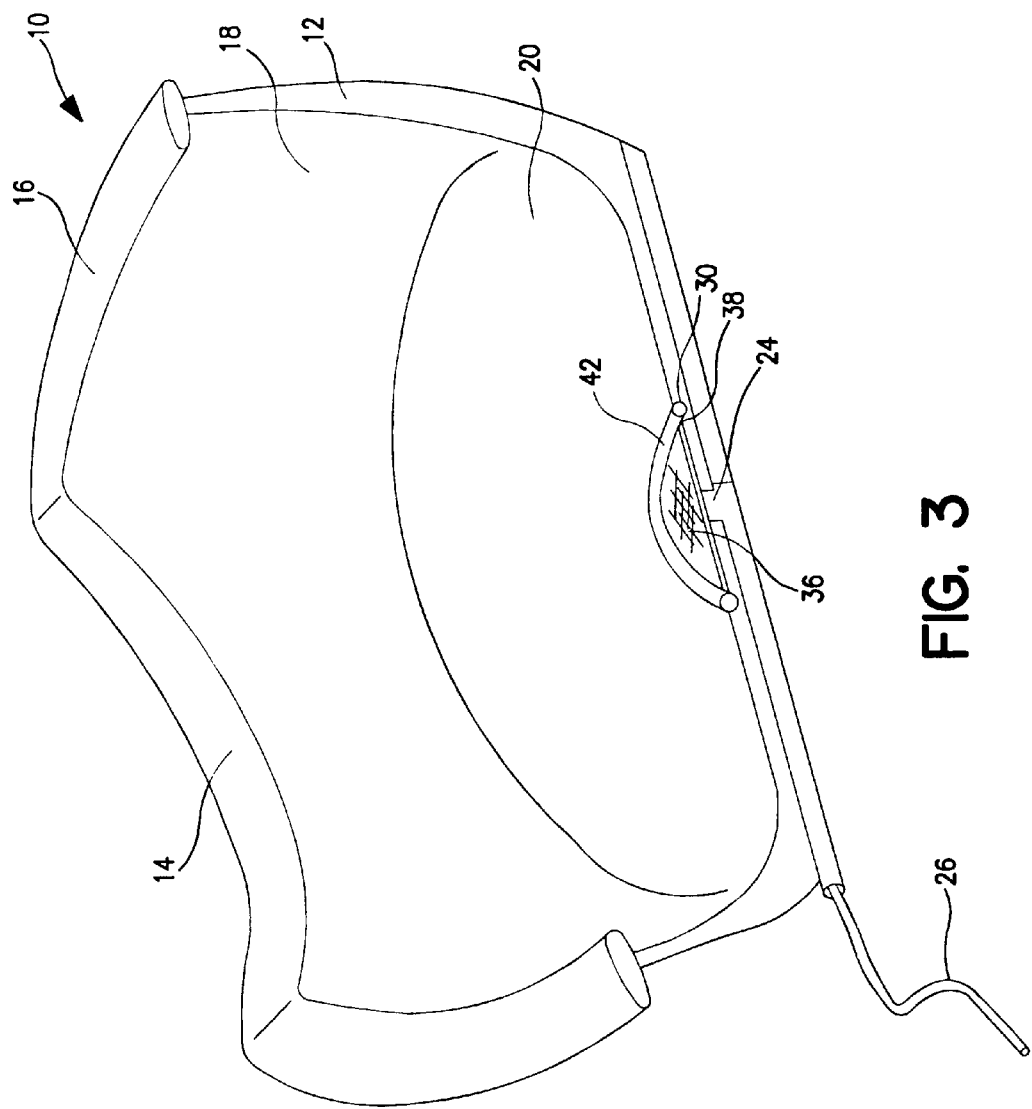
FIG. 3 is also a transverse cross-section of the basin of the invention, depicting use of a holder to secure a microfilter over a drainage hole, and omitting any use of a debris.

Alternatively, referring to FIG. 3, microfilter pad 36 may be placed within holder 42 which is placed in interior area of attachment side of screen 28. In further embodiments, microfilter pad 36 and holder 42 may be utilized by attachment to groove 30 without use of screen 28.

Figure 4:
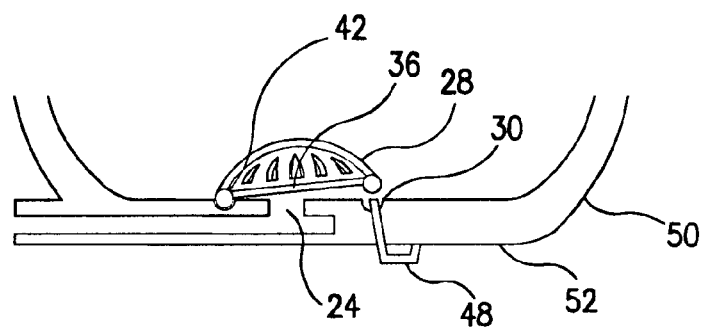
FIG. 4 illustrates a cross-section partial side view of the preferred basin of the invention, depicting a debris screen in place over the drainage hole in the base of the basin, and a microfilter in place under the debris filter, as well as a release member incorporated into the groove for disengaging the debris screen.

Referring to FIG. 4, release member 48 (e.g., a spring or lever release mechanism) may be incorporated within groove 30 for operation from exterior surface 50 of basin 10. This member allows a user to disengage screen 28 and/or microfilter pad 36 and holder 42 for potential cleaning or disposal without contacting the members.

It is preferred that the entire basin 10 and its components be disposable, however, embodiments wherein basin 10 may be cleaned are foreseen. Additionally, bottom 52 of exterior surface 50 should be sufficiently flat to stabilize basin 10 for use.

Figure 5:
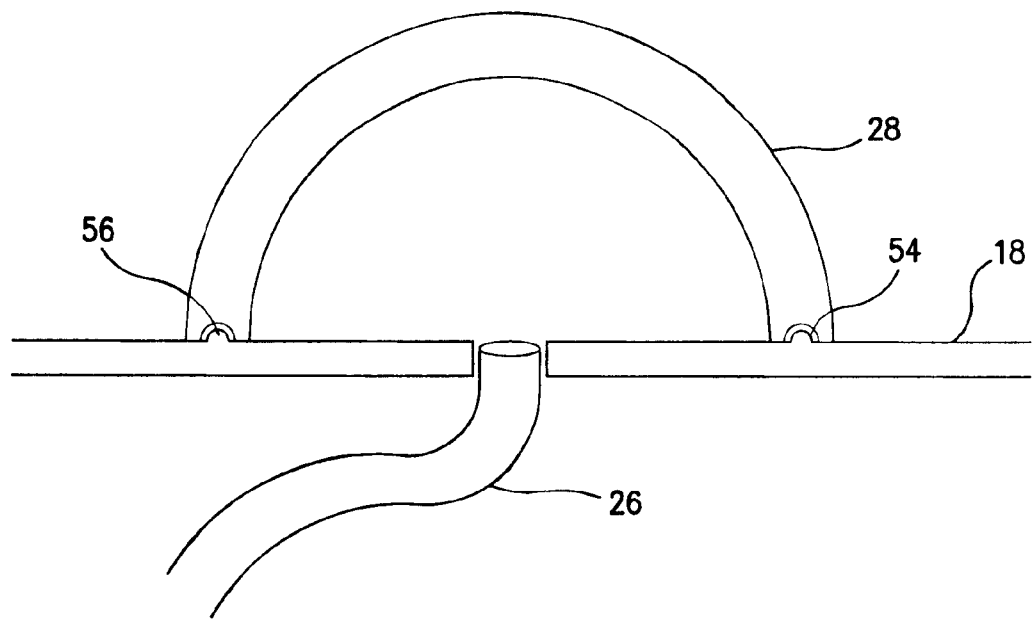
FIG. 5 illustrates a cross-section partial side view of the preferred basin of the invention, depicting use of an alternative form of attachment for the debris screen which may also be used to attach the holder.

Referring to FIG. 5, screen 28 and/or holder 40 may have surface grooves 54 for receipt of ridge 56 on interior surface 18 of basin 10.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A basin comprising:
   a unitary fluid and debris receptacle comprising a base, at least one seat in an upper surface of said receptacle, and side walls curved for increased gravity flow;
   a drainage hole extending through a bottom of said base;
   a filter covering said drainage hole, said filter comprising a screen and a microfilter pad;
   a holder wherein said microfilter pad is contained within said holder; and
   a member for removably retaining the holder on the seat.

2. The basin of claim 1 further comprising tubing connected to said drainage hole.

3. The basin of claim 1 wherein said screen comprises apertures between approximately 0.01 cm and approximately 1 cm in width.

4. The basin of claim 3 wherein said screen comprises apertures between approximately 0.01 cm and approximately 0.5 cm in width.

5. The basin of claim 1 wherein said microfilter pad comprises openings between approximately 0.0001 cm and approximately 0.1 cm in width.

6. The basin of claim 5 wherein said microfilter pad comprises openings between approximately 0.01 cm and approximately 0.05 cm in width.

7. The basin of claim 1 wherein said receptacle comprises a material selected from the group comprising plastic resins, stainless metals, and fiberglass.

8. The basin of claim 1 wherein said at least one seat is contoured.

9. The basin of claim 8 comprising two opposing contoured seats.

10. A combination of a basin as in claim 1 and recirculation means.

11. The basin of claim 10 wherein said recirculation means comprises an ultrasonic cleaner.

12. A basin comprising:
   a unitary debris and fluid receptacle, said receptacle comprising a base, at least two seats on opposing sides of an upper surface of said receptacle, and side walls curved for increased gravity flow;
   a drainage hole extending through a bottom of said base;
   a filter covering said drainage hole, said filter comprising a screen and a microfilter pad;
   a holder wherein said microfilter pad is contained within said holder; and
   a member for removably retaining the holder on the seats.

13. The basin of claim 12 further comprising tubing connected to said drainage hole.

14. The basin of claim 12 wherein said screen comprises openings between approximately 0.01 cm and approximately 1 cm in width.

15. The basin of claim 14 wherein said screen comprises openings between approximately 0.01 cm and approximately 0.5 cm in width.

16. The basin of claim 12 wherein said microfilter pad comprises openings between approximately 0.0001 cm and approximately 0.1 cm in width.

17. The basin of claim 16 wherein said microfilter pad comprises openings between approximately 0.01 cm and approximately 0.05 cm in width.

18. The basin of claim 12 wherein said receptacle comprises a material selected from the group comprising plastic resins, stainless metals, and fiberglass.

19. A combination of a basin as in claim 12 and a recirculation means.

20. The combination of claim 19 wherein said recirculation means comprises an ultrasonic cleaner.

21. The basin of claim 12 wherein at least one of sad seats is contoured.

* * * * *